United States Patent [19]
Shimazaki et al.

[11] Patent Number: 6,051,223
[45] Date of Patent: *Apr. 18, 2000

[54] METHOD OF IMPROVING SOLUBILITY OF TISSUE PLASMINOGEN ACTIVATOR

[75] Inventors: Yukio Shimazaki; Miyuki Kawashima; Masahiko Ishibashi, all of Mobara; Ryo Tanaka, Fujieda; Kiyoshi Sakai, Fujieda; Hisahiro Ishiwari, Fujieda, all of Japan

[73] Assignees: Mitsui Toatsu Chemicals Incorporated; Mochida Pharmaceutical Co. Ltd., both of Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/021,652

[22] Filed: Feb. 22, 1993

Related U.S. Application Data

[63] Continuation of application No. 07/580,913, Sep. 12, 1990, abandoned.

[51] Int. Cl.⁷ ................................. A61K 38/49
[52] U.S. Cl. ....................... 424/94.63; 424/94.64; 424/94.1
[58] Field of Search ............... 424/94.63, 94.64, 424/94.1; 435/219, 226; 436/69

[56] References Cited

U.S. PATENT DOCUMENTS

| | | | |
|---|---|---|---|
| 4,083,961 | 4/1978 | Dussourdd'Hinterland | 424/95 |
| 4,552,760 | 11/1985 | Murakami et al. | 424/94.1 |
| 4,818,690 | 4/1989 | Paques | 424/94.63 |
| 4,837,022 | 6/1989 | Kakimoto et al. | 424/94.64 |
| 4,898,826 | 2/1990 | Duffy et al. | 435/226 |
| 4,980,165 | 12/1990 | Isaacs et al. | 424/94.64 |

FOREIGN PATENT DOCUMENTS

| | | |
|---|---|---|
| 0198321 | 10/1988 | European Pat. Off. . |
| 59-51220 | of 0000 | Japan . |
| 60-158116 | of 0000 | Japan . |
| 60-158117 | of 0000 | Japan . |
| 60-181028 | of 0000 | Japan . |
| 60-184026 | of 0000 | Japan . |
| 61-236726 | of 0000 | Japan . |
| 61-236730 | of 0000 | Japan . |
| 62-120321 | of 0000 | Japan . |
| 62-123130 | of 0000 | Japan . |
| 62-164632 | of 0000 | Japan . |
| 62-234030 | of 0000 | Japan . |
| 62-26234 | of 0000 | Japan . |
| 62-292729 | of 0000 | Japan . |
| 62-36332 | of 0000 | Japan . |
| 62-59221 | of 0000 | Japan . |
| 62-81326 | of 0000 | Japan . |
| 64-34922 | of 0000 | Japan . |

*Primary Examiner*—Jean C. Witz
*Attorney, Agent, or Firm*—Nixon & Vanderhye

[57] ABSTRACT

A thrombolytic composition containing tissue type plasminogen activator or a derivative thereof in combination with an anionic polymer or a salt thereof and an amine compound or a salt thereof or in combination with an anionic polymer or a salt thereof, an amine compound and an acid or a salt thereof. The composition is an aqueous solution or a lyophilized preparation which can be stably dissolved on dilution at near neutral pH in both pharmaceutical solutions having high salt concentrations, such as physiological saline, and pharmaceutical solutions having low salt concentrations, such as a 5% glucose solution. Clinically useful products for infusion or injection are prepared to be used at a pH near neutral.

10 Claims, 4 Drawing Sheets

6,051,223

METHOD OF IMPROVING SOLUBILITY OF TISSUE PLASMINOGEN ACTIVATOR

This is a continuation of application Ser. No. 07/580,913, filed Sep. 12, 1990, now abandoned.

BACKGROUND OF THE INVENTION

1. Field of the Invention

The present invention relates to a thrombolytic composition containing tissue type plasminogen activator (t-PA) or a derivative thereof as a major active component.

2. Description of the Prior Art t-PA has become the object of much attention as a novel plasminogen activator for pharmaceutical use, because, unlike conventionally known urokinase, t-PA has strong affinity to fibrin and high thrombolytic activity and, in particular, single-chain t-PA causes fewer side effects. Recently, it has become possible to use t-PA as a thrombolytic agent practically in medicine due to the development of procedures for producing t-PA in large quantities using cell culture techniques as well as gene recombination techniques.

However, t-PA, a protein having an isoelectric point in the range of 6–8, is extremely insoluble at pHs near the isoelectric point so that it became necessary to solve the problem with regard to the solubility of t-PA in order to formulate t-PA as a medicament. For this purpose, various investigations regarding the t-PA preparation have been conducted to improve the solubility of t-PA, and thus a good deal of information has been provided.

In general, known methods for improving the solubility of proteins include (1) dissolving the protein at an acidic or alkaline pH apart from the isoelectric point of the protein, (2) dissolving the protein at a pH near the isoelectric point of the protein in a solution with an increased salt concentration or ionic strength, and (3) dissolving the protein with the aid of a dissolution auxiliary agent specific to the protein.

Known methods to improve the solubility and stability of t-PA in preparing pharmaceutical t-PA formulations are characterized in that (1) acidic pHs apart from the isoelectric point of t-PA are used (for example, Japanese Patent Laid-open No. 26234/1987 and Japanese Patent Laid-Open No. 36332/1987), (2) the protein is diluted in a solution solely with a t-PA stabilizing agent, in which none of particular dissolution auxiliary agent is added and a salt in a relatively high concentration is used (for example, Japanese Patent Laid-open No. 292729/1987) or (3) a dissolution auxiliary agent such as a basic amino acid (e.g., arginine) is added (for example, Japanese Patent Laid-open No. 81326/1987, Japanese Patent Laid-open 120321/1987, and Japanese Patent Laid-open 164632/1987).

The above-mentioned pharmaceutical methods for the preparation of t-PA improve the solubility of t-PA in different ways but have undesirable disadvantages from a pharmaceutical point of view.

Specifically, (1) it is desirable to prepare pharmaceuticals for injection near the pH of blood (pH 7.4) and an acid solution may cause hemolysis so that a preparation at a pH near neutral is more preferable than that at an acidic pH; (2) a solution with a high salt concentration is not preferable for injection because of its high osmotic pressure; furthermore, in a preparation in which large quantities of salt are added in advance to prepare a lyophilized preparation, the osmotic pressure is increased extremely high when later diluted in physiological saline, which is generally used for dilution; furthermore, considering the use of t-PA as a medicament, it is not desirable to administer sodium ion in large doses; and (3) compounds known as auxiliary agents for the dissolution of t-PA today have the following disadvantages: i) when used alone, none of the agents can dissolve t-PA satisfactorily so that it is necessary to increase the salt concentration to some extent, and ii) when a lyophilized preparation is reconstituted and then diluted exceeding a certain dilution extent with a low salt diluent, the auxiliary agent for dissolution is also diluted at the same time, and the dissolution effect is thus lessened, resulting in precipitation of t-PA in some cases. Consequently, there arises such an inconvenience that the t-PA preparation is well dissolved in physiological saline, which is an infusion for injection with a high salt concentration, but hardly dissolved in a 5% glucose solution which is also generally used as an infusion for injection with a low salt concentration. t-PA is administered mostly in cases of an urgent need and, in such cases, alternative is usually limited for an infusion to reconstitute a lyophilized t-PA preparation or to dilute it; for this reason, it has been desired to develop a pharmaceutical preparation suitable for use in injection, which is easy to dissolve both in physiological saline and in a 5% glucose solution over a broad range of t-PA concentrations while providing an appropriate salt concentration and osmotic pressure. Further, the term "salt" in a salt concentration as used in this specification means mainly chloride; however, it also includes other salts such as amino acids or other compounds in the form of salts which are clinically acceptable.

SUMMARY OF THE INVENTION

An object of the present invention is to provide a thrombolytic composition having an improved t-PA solubility in a solution with low as well as high salt concentrations over a broad range of t-PA concentrations. Another object of the present invention is to provide a thrombolytic composition in which the solubility of t-PA near the neutral pH is improved. Another object of the present invention is to provide a t-PA preparation in which stability is improved.

In order to solve the above-mentioned problem, the present inventors have found that t-PA is dissolved in a solution at both high and low salt concentrations on mixing t-PA with an anionic polymer, namely an anionic polymer or a salt thereof and an amine compound or a salt thereof, or with an anionic polymer or a salt thereof, an amine compound and an acid or a salt thereof.

The present invention provides a thrombolytic composition comprising t-PA or a derivative thereof in combination with an anionic polymer or a salt thereof and an amine compound or a salt thereof, or with both an anionic polymer or a salt thereof and an amine compound and an acid or a salt thereof.

According to the present invention, a pharmaceutical solution containing t-PA at such a high concentration that conventional techniques cannot be attained, can now be obtained, in which a t-PA preparation is well dissolved at a pH near neutral which is the isoelectric point of t-PA, in a diluent at both low and high salt concentrations suited for parenteral administration, such as distilled water for injection, a 5% glucose solution, physiological saline or an infusion for injection, which are conventionally used diluents. The dilution is almost unlimited and t-PA, in forms of both lyophilized and dissolved, is stable.

Thus, the present invention is preferably applicable to pharmaceutical preparations of t-PA, particularly at pHs near neutral.

DETAILED DESCRIPTION AND THE PREFERRED EMBODIMENTS

Figure 1:
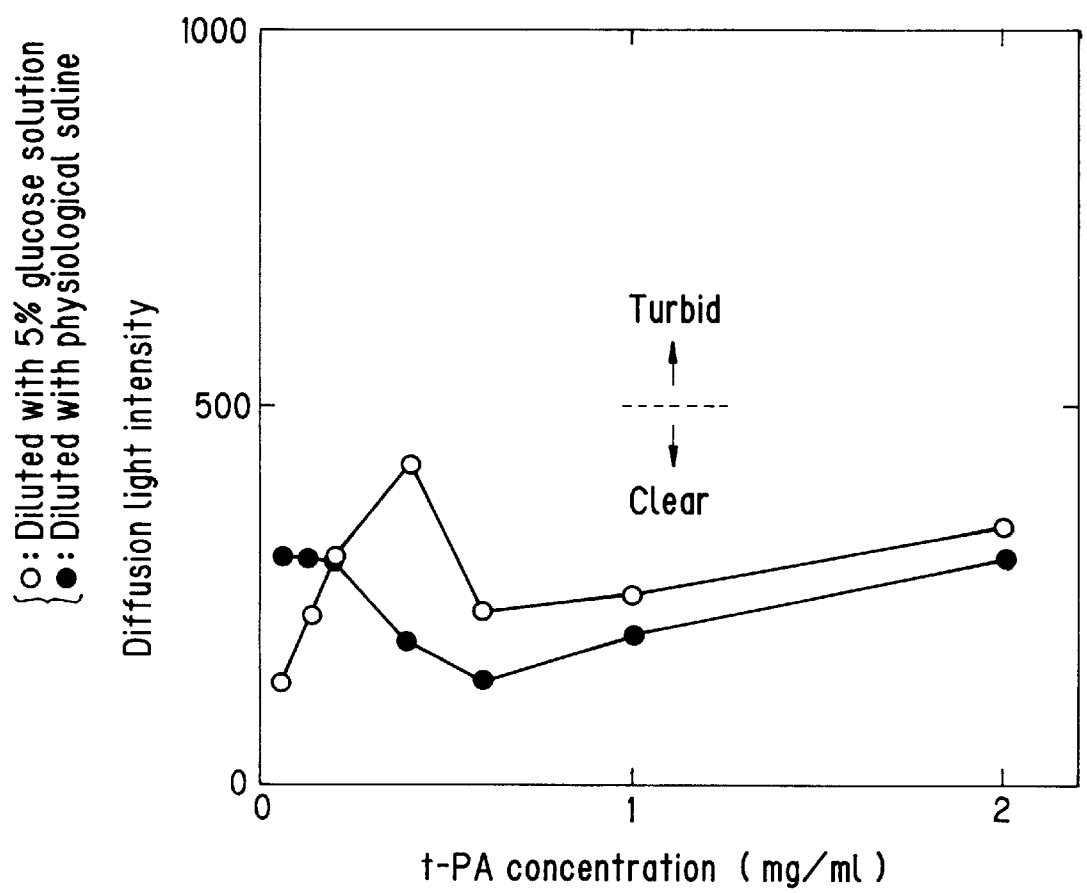
FIG. 1 is a graph showing the turbidity (diffusion light intensity) of t-PA solutions diluted at different t-PA concentrations, in which sodium heparin, arginine and sulfuric acid are added to t-PA and the pH of the resultant solution is adjusted to 7.5 (see Example 7).

The t-PA or a derivative used in accordance with the invention is not restricted and includes proteins having t-PA activity regardless of the manner of production. Examples of the t-PA and its derivatives include t-PA obtained by extraction and purification from human or animal cells; t-PA obtained by cultivating cells derived from human or animal tissues and by extracting the cells or cell culture, thereby purifying t-PA; t-PA or a derivative thereof obtained using recombinant DNA techniques by cultivating cells which carry the incorporated nucleotide sequence of t-PA gene or a modified nucleotide sequence of t-PA gene using known recombinant DNA techniques so as to exert t-PA activity when expressed, by extracting the cells or the cell culture, thereby purifying t-PA; and a t-PA derivative in which purified t-PA or a derivative thereof is chemically modified. Examples of modifications of the nucleotide sequence coding for t-PA or a derivative thereof include mutation in which portions of amino acids or polypeptides are deleted or replaced and hybridization with other proteins (e.g., L. Hansen et al. J.Biol. Chem. 263, 15713–15719 (1988)). Examples of the cells, which incorporate the nucleotide sequence of the t-PA gene or a modified nucleotide sequence of the t-PA gene using known recombinant DNA techniques so as to exert t-PA activity when expressed, include microorganisms such as strains of *Escherichia coli*, *Bacillus subtilis* and yeasts, or cells of animals such as Chinese hamsters, mice and humans.

The t-PA used in the present invention may be single-chain t-PA, double-chain t-PA or a mixture of the two.

Unless otherwise specified, t-PA used in the present invention implies single- or double-chain t-PA and derivatives thereof or a mixture thereof.

In the present invention, where thrombolytic composition is in an aqueous solution, the pH of the solution is weekly acid, neutral, weakly alkaline, or alkaline, and is preferably in the range ofpH 5–9, more preferably in the range of pH 6–8. However, the pH range of the solution depends upon the individual anionic polymers, amine compounds and salts thereof used, and thus the scope of the present invention is not restricted by the pH of the solution.

Examples of anion residues of anionic polymers used in the present invention include carboxyl, carboxymethyl, sulfuric and phosphoric groups. On the other hand, examples of polymer backbones of anionic polymers include sugars such as sugar alcohols, cellulose, amylose, amino acids and nucleic acid bases, preferably having a molecular weight of approximately 1,000–1,000,000.

Examples of anionic polymers containing these anion residues and polymer backbones in combination are carboxymethyl ion-exchangers such as carboxymethylamylose and carboxymethylcellulose, acidic polysaccharides such as arginic acid, mucosaccharide sulfates such as dextran sulfate, chondroitin sulfate, chondroitin sulfate A, chondroitin sulfate B, chondroitin sulfate C, chondroitin sulfate D, chondroitin sulfate E, heparin, kerato sulfate, keratane sulfate and heparitin sulfate, polyamino-acid such as poly-L-glutamic acid and nucleic acids. Furthermore, example of salts of these anionic polymers include salts of sodium, potassium, calcium or the like.

These anionic polymers or the salts thereof are used by themselves or in combinations of two or more of them.

An amount of an anionic polymer or a salt thereof is preferably 25 micrograms or more, more preferably 100 micrograms or more per 1 mg of t-PA to be dissolved, while the preferable upper limit of the amount of an anionic polymer is 100 mg per 1 mg of t-PA to be dissolved. If the amount is too small, t-PA may not be dissolved satisfactorily; on the contrary, if the amount is too large, there may be difficulties in the solubiilty of the anionic polymer itself.

An amine compound is more convenient to use in its salt form in dissolving t-PA than in its non-salt form. A non-salt amine compound is, however, used in combination with an acid or a salt thereof as described below.

Examples of amine compounds used in the present invention include ethanolamines such as monoethanolamine, diethanolamine and triethanolamine, basic amino acids such as arginine, lysine and histidine, amine polymers such as polyethyleneimine, and trishydroxymethylaminomethane. Furthermore, examples of salts of these amine compounds include chloride, sulfate and phosphate.

These amine compounds or salts thereof may be used by themselves or in combinations of two or more types.

The amine compound salts can be preferred in view of their availability on the market unless there are difficulties in handling them. However, in the case of salts such as basic amino acid phosphate or sulfate, salts of polyethyleneimine or trishydroxymethylaminomethane and the like, which are not readily available on the market or involve difficulties in handling due to their absorption of moisture, it is preferred to have the acids or their salts described below present along with amine compounds in the form of non-salts.

An amount of an amine compound or a salt thereof is typically in the range of 20 micromoles–10 mmoles, preferably 50 micromoles–500 micromoles, per 1 mg of t-PA to be dissolved. If the amount is too small, t-PA may not be dissolved satisfactorily; on the other hand, if the amount is too large, the amount of amine compounds may cause adverse physiological effects such as toxicity and cannot be used for medicinal preparations.

Examples of acids which are particularly effective when used with a non-salt amine compound include oxalic acid, hydrochloric acid, sulfuric acid, phosphoric acid, pyrophosphoric acid, citric acid, tartaric acid, malic acid, maleic acid, glucuronic acid, glutaric acid, lactic acid, adipic acid and ascorbic acid. The salts of these acids suitable for use are sodium salts, potassium salts, calcium salts and the like.

A polyvalent acid or a salt thereof is preferable, in particular sulfuric acid, phosphoric acid, pyrophosphoric acid and citric acid and salts thereof are preferable.

The amount of an acid or salt used is usually in the range of 20 micromoles–10 mmoles, preferably 50 micromoles–500 micromoles, per 1 mg of t-PA to be dissolved. If the amount is too small, the solubility of t-PA in a solution having low concentrations of salts is insufficient. If the amount is too large, the improvement in the solubility of t-PA due to anionic polymer becomes insufficient and, as a medical preparation for injection, salt concentrations and osmotic pressures become too high.

Salts themselves such as NaCl or the like, additives in salt form such as amino acid or EDTA described below in the form of salts, or salts of acids or alkalines which are used for adjusting pH as described below, may also be present.

The amount of salt to be used in the present invention, excluding the anionic polymers and salts thereof, amino compounds and salts thereof, acid and salts thereof, for example, is preferably 200 micromoles or less, more preferably 10 micromoles or less, per 1 mg of t-PA, considering the salt concentration and osmotic pressure ratio when t-PA is administered. The amount is not particularly restricted.

Aqueous solutions of the, thrombolytic composition of the present invention may be prepared, for example, in a manner in which a solution is prepared with an anionic polymer or a salt thereof and an amine compound or a salt thereof or with an amine compound and an acid or a salt thereof, the pH of the solution adjusted in advance to near neutral, and then the resultant solution-added to a solution in which t-PA is dissolved at a pH different from the isoelectric point of t-PA. Furthermore, the anionic polymer or a salt thereof and the amine compound or a salt thereof both in solid form together with an acid or a salt thereof are dissolved in the above-mentioned t-PA solution and the pH of the resultant solution is readjusted to prepare the t-PA aqueous solution by adding acids such as hydrochloric acid or sodium hydroxide, as necessary. Furthermore, an aqueous t-PA solution can be obtained by dissolving ingredients other than the t-PA, adjusting the pH of the resultant solution, and then adding t-PA to the solution in a desired concentration.

A concentration of t-PA in an aqueous t-PA solution is not particularly limited and the t-PA is stably dissolved in the range of from 0.001 to 10 mg/ml (or from 600 to 6,000,000 IU/ml). For use as an infusion for injection or the like, a preferred concentration in general is from 0.01 to 5 mg/ml (or from 6,000 to 3,000,000 IU/ml). Using this aqueous t-PA solution, the solubility can preferably be maintained at various t-PA concentrations for clinical use in a solution with a high salt concentration, such as physiological saline, or in a solution with a low salt concentration, such as a 5% glucose solution. Using the aqueous t-PA solution, a pharmaceutical solution having the appropriate osmotic pressure can be easily prepared at a desired t-PA concentration regardless of its salt concentration.

To obtain t-PA in the form of a lyophilized preparation, for example, an aqueous t-PA solution prepared by any of the above-mentioned methods is filtrated with a filter to remove cells and then the resultant filtrate is dispensed into sealable containers such as vials and ampoules to be lyophilized.

An amount of t-PA in the lyophilized preparation may be 0.1–10 wt %. The lyophilized preparation can be used in the same manner as with the above-mentioned aqueous solution and reconstituted at use with the appropriate parenteral carrier or diluent.

Furthermore, if necessary, in order to prevent polymerization of t-PA molecules and adhesion of t-PA to the containers, a surfactant such as Tween 80, a chelating agent such as EDTA to eliminate the effect of metal ions to the protein, proteins such as albumin and gelatin and sugars such as dextran as a stabilizer, and furthermore a excipient such as mannitol and lactose (effective when used in a lyophilized preparation) may be added alone or in combination.

In either the form of an aqueous solution or in the form of a lyophilized preparation according to the present invention, a t-PA pharmaceutical solution can be stably formulated at a pH of from 5 to 9, regardless of salt concentrations, and thus applicable for clinical use.

EXAMPLES

The present invention will be described more specifically in the following Examples; however, it is to be understood that the Examples are not intended as a definition of the limits of the invention.

The t-PA used in the Examples was t-PA, a single-chain or double-chain t-PA or an admixture of the two, which was obtained by expressing the structural gene of t-PA in a cell culture using recombinant DNA techniques and by purifying t-PA from the culture fluid. The single-chain t-PA and the double-chain t-PA were respectively obtained by specifically purifying the culture fluid; the admixture was obtained by purifying the culture fluid without separating a single-chain t-PA from a double-chain t-PA.

Turbidity of the solution was observed mainly by the naked eye; diffusion light intensity of the solution was measured to estimate the turbidity quantitatively. Generally, the solution was judged to be clear when the diffusion light intensity was 500 or less under the conditions of the measurement used.

Determination of the concentrations of the protein dissolved in the solution was carried out for simple estimation of t-PA recovery. For this determination, after centrifugation of a sample, the resultant supernatant was subjected to quantitative determination of protein concentration by the method of Lowry or by ultraviolet absorption measurement. Unless otherwise stated, the t-PA recovery was calculated based on the result of this determination.

Activity of t-PA dissolved in a solution was determined by the clot-lysis-time method in which a sample to be measured was centrifuged and the resultant supernatant was measured according to the method described by Gaffney and Curtis (P. J. Gaffney and A. D. Curtis, 1985, Thromb. Haemastas, 53, 134, 1985) using an internal t-PA standard which is prepared referring to WHO t-PA as a standard.

Reference Example 1

To a weakly acid solution of single-chain t-PA were added 0.5 mg of sodium heparin or 19.5 mg of monoethanolamine chloride and different amounts of sodium chloride, and then, the pH of the individual solutions was adjusted to the range near the neutral (pH 6.5 to 7.5). Subsequently, the solution is diluted with a 5% glucose solution adjusting the t-PA concentration to 0.2 mg/ml.

Figure 4:
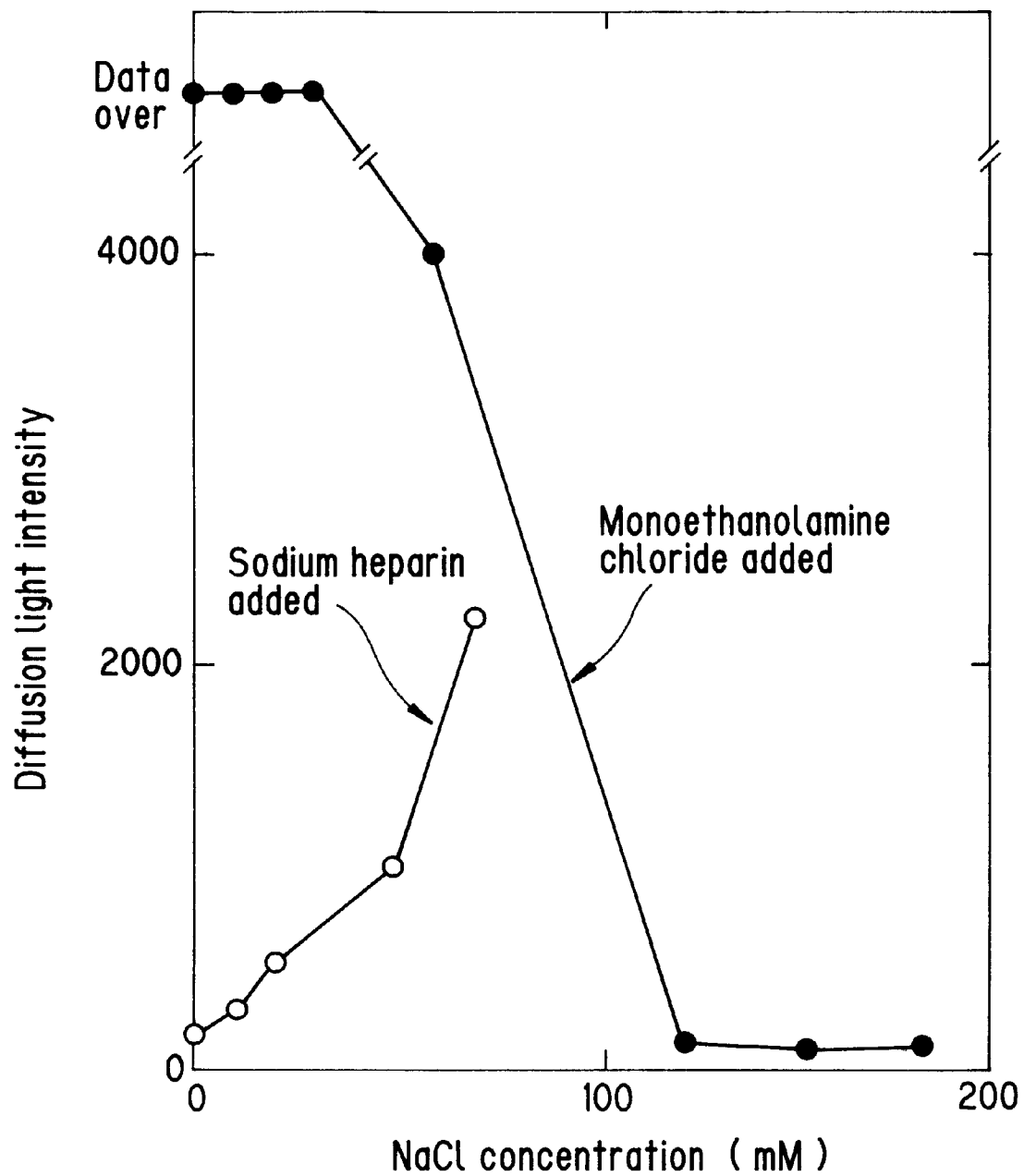
FIG. 4 is a graph demonstrating the effect of salt concentrations on the solubility of t-PA in a solution to which sodium heparin or monoethanolamine chloride is added respectively (see Example 1). NaCl concentrations shown in this Figure are those determined when diffusion light intensities are measured.

As a result, as shown in FIG. 4, in samples to which sodium heparin was added, t-PA was completely dissolved without sodium chloride, but with the increase in salt concentration, an increase in turbidity was observed, which indicated a decrease in solubility. In samples to which monoethanolamine chloride was added, in contrast, t-PA was hardly dissolved without sodium chloride, but with the increase in salt concentration, a decrease in turbidity was observed, which indicated a increase in solubility. Further, in order to completely dissolve t-PA in a sample containing monoethanolamine chloride, sodium chloride at a concentration near that of physiological saline (0.9% or 150 mM) had to be added.

Furthermore, the above-mentioned inhibitory and stimulative effects on the solubility of t-PA were similarly observed when other anionic polymers or salts thereof, or amine compounds and salts thereof were added alone, respectively. These effects were similarly observed independently whether the t-PA was signle-chain or double-chain t-PA.

From these results, it was found to be difficult to prepare t-PA containing compositions which can dissolve both in a diluent or an infusion for injection with a low salt concentration such as a 5% glucose solution and in a diluent or an infusion for injection with a high salt concentration such as physiological saline, in the case where an anionic polymer or a salt thereof or an amine compound or a salt thereof was added alone in an attempt to dissolve t-PA at a pH near neutral, which is the isoelectric point of t-PA.

Reference Examples 2 to 5 and Examples 1 to 4

To a weakly acid solution containing single-chain t-PA and double-chain t-PA at a ratio of 15:85 were added a salt of anionic polymer, sodium heparin or sodium dextran sulfate and a salt of amine compound, lysine chloride or monoethanolamine chloride, individually, or the above-mentioned salt of anionic polymer and a salt of an amine compound in combination, and then the pH of the resultant solution was adjusted near neutral (pH 6.5 to 7.5) and the t-PA concentration was adjusted to 4 mg/ml. Subsequently, the solution was diluted with physiological saline or a 5% glucose solution to make the t-PA concentration 0.2 mg/ml.

As a result, as shown in Table 1, it was confirmed that, as observed in Reference Example 1 described above, (1) t-PA was soluble in the 5% glucose solution but insoluble in the physiological saline when the anionic polymer salt was added alone (Reference Examples 2 and 3) and that (2) t-PA was soluble in physiological saline but insoluble in the 5% glucose solution when the salt of amine compound was added alone (Reference Examples 4 and 5). However, t-PA was soluble in both the physiological saline and the 5% glucose solution when the anionic polymer salt and the amine compound were both added (Examples 1 to 4).

These studies confirmed that, by fully utilizing both the advantages of using anionic polymer salts, which improve t-PA solubility only in solutions having relatively low salt concentrations, and of using amine compounds, which improve t-PA solubility only in solutions having relatively high salt concentrations, both the disadvantages of amine compounds in low salt concentrations and of anionic polymer in high salt concentrations can be overcome.

From these results, it was revealed that a t-PA preparation, which is soluble both in physiological saline with a high salt concentration and in a glucose solution without salt in the form of a t-PA aqueous solution, can be prepared by adding in combination a salt of an anionic polymer, which effectively helps dissolving t-PA at a low salt concentration, and a salt of amine compound, which effectively helps dissolving t-PA at a high salt concentration.

Furthermore, it is evident that a non-salt composition of an anionic polymer or an amine compound exerts similar effects.

Example 5

To a weakly acid solution of single-chain t-PA were added sodium chondroitin sulfate together with monoethanolamine chloride or sodium chondroitin sulfate together with arginine and sulfuric acid, and the t-PA concentration of the resultant solution was adjusted to 4 mg/ml after adjusting the pH to 6.0, 7.5 or 9.0. Then the solution was diluted with physiological saline or a 5% glucose solution to make the t-PA concentration 0.2 mg/ml.

As a result, as shown in Table 2, solutions having a t-PA concentration of 4 mg/ml and diluted solutions having a t-PA concentration of 0.2 mg/ml were clear and the turbidities thereof were low at any adjusted pH. The protein recovery rates in the supernatants after centrifugation were essentially 100%.

From these results, it is revealed that t-PA prepared in the form of an aqueous solution by adding a salt of anionic polymer together with a salt of amine compound or a salt of anionic polymer and an amine compound together with an acid to dissolve t-PA was effective (1) in a t-PA solution with a relatively high salt concentration and (2) in a range of weakly acidic to weakly alkaline pHs.

Furthermore, it is evident that the non-salt composition of an anionic polymer or an amine compound exerts similar effects.

Example 6

An aqueous solution of t-PA (4 mg/ml) prepared in the same manner as described in Example 5 was lyophilized and then reconstituted and diluted with physiological saline or a 5% glucose solution to give a t-PA concentration of 0.2 mg/ml. Consequently, a similar result as shown in table 2 in Example 5 was obtained.

From this, it was revealed that a t-PA composition can be obtained by adding a salt of anionic polymer and a salt of amino compound or by adding a salt of anionic polymer, a salt of amine compound and an acid, which resulted in sufficient dissolution of t-PA not only in the form of a solution but also in the case where a lyophilized preparation is reconstituted.

Examples 7 and 8

To a weakly acid solution containing single-chain t-PA and double-chain t-PA at a ratio of 15:85 were added 5 mg of sodium heparin, 26.1 mg of arginine and 14.7 mg ofsulfuric acid per 1 mg of t-PA (Example 7) or 5 mg of sodium chondroitin sulfate and 19.5 mg ethanolamine chloride per 1 mg of t-PA (Example 8), and the t-PA concentration was adjusted to 4 mg/ml and the pH of the resultant solution was adjusted to 7.5. Then the solution was diluted with physiological saline or a 5% glucose solution to give a t-PA concentration of 2.0 mg/ml to 5 micrograms/ml.

Figure 2:
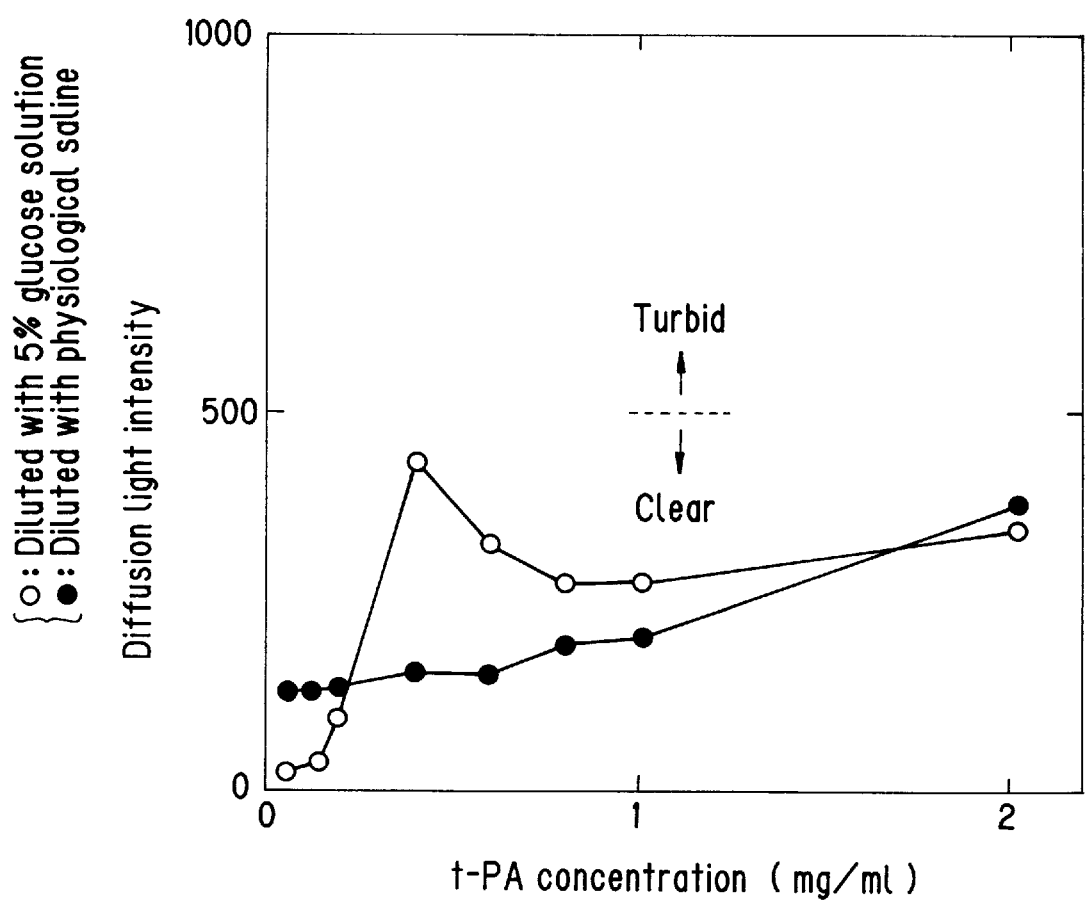
FIG. 2 is a graph showing the turbidity of t-PA solutions diluted at different concentrations, in which sodium chondroitin sulfate and ethanolamine chloride are added to t-PA and the pH of the resultant solution is adjusted to 7.5 (see Example 8).

As a result, as shown in FIG. 1 (Example 7) and FIG. 2 (Example 8), the solution was clear and the turbidity was sufficiently low in all of the combinations of the additives regardless of the t-PA concentration. Furthermore, t-PA recovery in the supernatant after centrifugation was 95% or more in all cases.

From these observations, it is revealed that the composition obtained by mixing t-PA with a salt of an anionic polymer and an amine compound and an acid or with a salt of anionic polymer and a.salt of amine compound has excellent solubility in such a wide range of the t-PA concentration as from at least 4 mg/ml to 5 micrograms/ml in both a 5% glucose solution and physiological saline and can be dissolved sufficiently when diluted at a t-PA concentration practically used in clinical medicine.

Example 9

In order to find the most appropriate pH for t-PA dissolution, to a weakly acid solution of single-chain t-PA were added 5 mg sodium chondroitin sulfate together with 19.5 mg of monoethanolamine chloride, the pH of the resultant solution was adjusted with hydrochloric acid or sodium hydroxide, and then the t-PA concentration was adjusted to 4 mg/ml. Subsequently, the solution was diluted with physiological saline or a 5% glucose solution to make the t-PA concentration 0.2 mg/ml.

Figure 3:
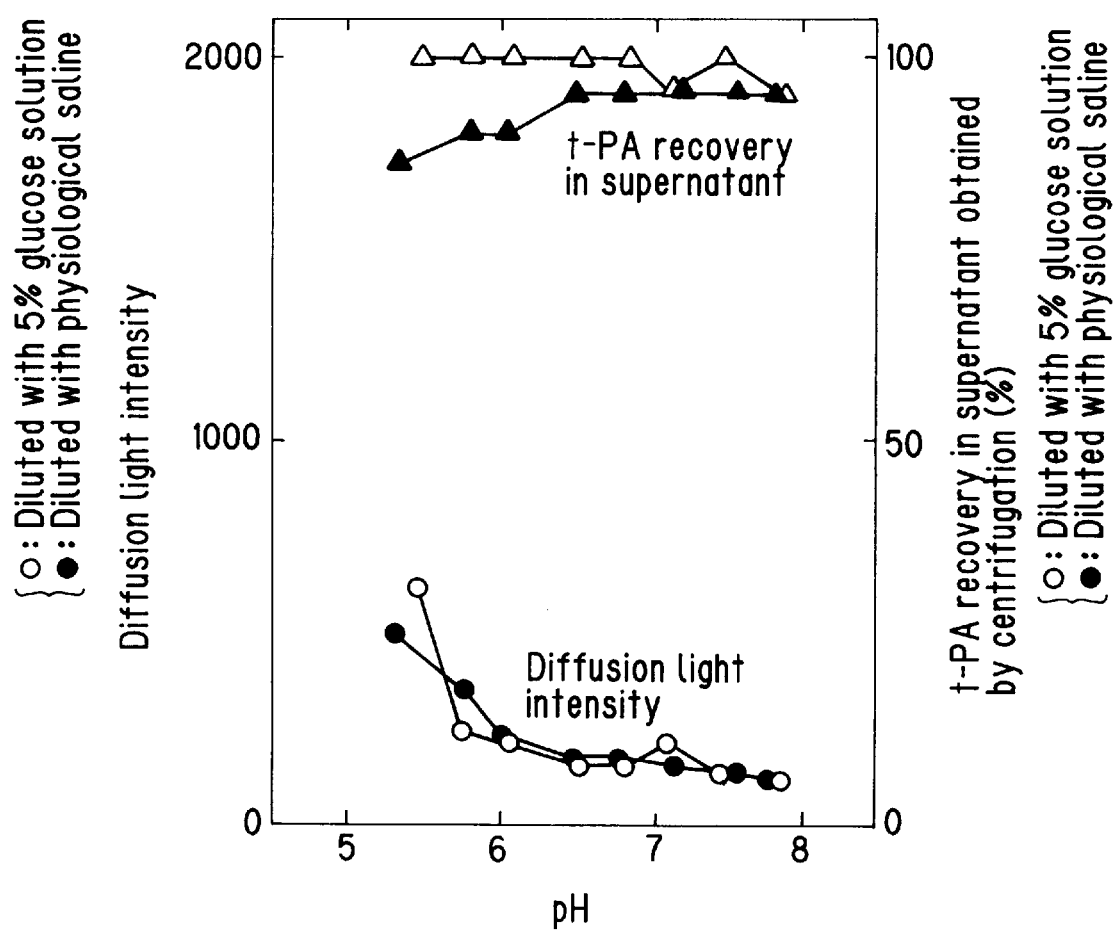
FIG. 3 is a graph demonstrating the effect of pH on the solubility of t-PA in a solution also containing sodium chondroitin sulfate and monoethanolamine (see Example 9). The pH values given in this Figure are practical measurements when t-PA is diluted at a concentration of 0.2 mg/ml with physiological saline or a 5% glucose solution.

As a result, as shown in FIG. 3, in the pH range between 6 and 8, whether the diluent was physiological saline or a 5% glucose solution, t-PA was completely dissolved and t-PA recovery in the supernatant obtained by centrifugation was nearly 100%. However, it was observed that t-PA was poorly dissolved in a solution with a pH 5.5 or lower than in a solution with the pH 6–8.

From this result and the result shown in Table 2, the most appropriate pH for dissolution of the composition in which t-PA was mixed with a salt of anionic polymer and a salt of amine compound in combination was considered to be 6–8.

Example 10

In the case where t-PA was mixed with neither an anionic polymer or a salt thereof but with an amine compound or a salt thereof or an amine compound and an acid, t-PA solubility is not satisfactory when the salt concentration was low, namely in a 5% glucose solution with a high dilution rate. In order to estimate the necessary amount of a salt of anionic polymer, 5,000,000 IU (9.1 mg) of t-PA were mixed with 287.4 mg of arginine, 165.1 mg of sulfuric acid, lmg of Tween 80 and an different amount of sodium chondroitin sulfate, the pH of the mixed solution was adjusted to 7.0 with sodium phosphate and sodium hydroxide and the resultant solution was lyophilized to prepare a pharmaceutical preparation. This preparation was reconstituted with a 5% glucose solution and diluted. The diluted solution was observed with the naked eye to investigate the effect of sodium chondroitin sulfate on the solubility of t-PA.

As a result, as shown in Table 3, in the preparation without sodium chondroitin sulfate, the solution was turbid when t-PA was diluted at a concentration of less than 50,000 IU/ml. However, on addition of 0.022 mg of sodium chondroitin sulfate per 1 mg of t-PA, the turbidity was fairly cleared and further on addition of more than 0.11 mg of sodium chondroitin sulfate per 1 mg of t-PA, sufficient solubility was attained even at a low salt concentration.

Example 11

In order to investigate the effects on the physical properties of t-PA of adding a salt of an anionic polymer together with an amine compound to t-PA, sodium chondroitin sulfate and arginine chloride or monoethanolamine chloride in combination were added to a weakly acid solution containing single-chain t-PA, the pH of the resultant solution was adjusted and then the solution was diluted with physiological saline or a 5% glucose solution at concentrations as shown in Table 4.

As a result, no difference was observed between the test samples and the control samples without the additives (in which the t-PA sample was dissolved in a weakly acid solution since it was impossible to dissolve t-PA near neutral pH without such additives), regarding the physico-chemical properties of t-PA, such as fibrinolytic activity per unit of protein examined by the clot-lysis-time method (Table 4), activity to decompose a synthetic substrate (for example S-2288 and S-2366) with or without treating t-PA with plasmin to cleave into two chains, the ratio of single-chain content degraded products or polymers investigated by sodium dodecyl sulfate polyacrylamide electrophoresis. These results thus indicate that when a salt of an anionic polymer and a salt of amine compound were added together, these additives had no effect on the physicochemical properties of t-PA. It is evident that similar effects could be observed alternatively using non-salt compounds of anionic polymers and/or amine compounds.

Example 12

A solution of t-PA (2 mg/ml) prepared in the same manner as described in Example 5 was allowed to stand at 37° C. for 24 hours. After the standing, no change was observed in regard to the turbidity of the solution, the recovery of t-PA in the supernatant after centrifugation or, furthermore, the physicochemical properties shown in Example 11.

Consequently, it has been revealed that a composition obtained by mixing t-PA with a salt of an anionic polymer and a salt of amine compound and a composition obtained by mixing with a salt of anionic polymer, a amine compound and an acid were sufficiently stable and caused no change in t-PA solubility in the form of a solution even under such experimental conditions that is more severe than practical ones inclinical medicine.

Experiment 13

| t-PA | 50,000,000 IU |
|---|---|
| Sodium heparin | 500 mg |
| Monoethanolamine chloride | 1950 mg |
| Tween 80 | 25 mg |
| Lactose | 500 mg |

The ingredients above, except t-PA, were dissolved in distilled water for injection and the pH of the solution was adjusted to 7.6 by adding sodium hydroxide. To the solution, t-PA was added and then distilled water for injection was added to make the total volume 25 ml. After aseptic filtration, the resulting solution was dispensed into vials, 2.5 ml each, and then lyophilized to prepare a thrombolytic composition.

Experiment 14

| t-PA | 50,000,000 IU |
|---|---|
| Sodium heparin | 500 mg |
| Lysine chloride | 910 mg |
| Tween 80 | 25 mg |
| Lactose | 500 mg |

The ingredients above, except t-PA, were dissolved in distilled water for injection and the pH of the solution was adjusted to 7.2 by adding sodium hydroxide. To the solution, t-PA was added and then distilled water for injection was added to make the total volume 25 ml. After aseptic filtration, the resulting solution was dispensed into vials, 2.5 ml each, and then lyophilized to prepare a thrombolytic composition.

Example 15

| | |
|---|---|
| t-PA | 50,000,000 IU |
| Sodium heparin | 500 mg |
| Arginine chloride | 1050 mg |
| Tween 80 | 25 mg |
| Lactose | 500 mg |

The ingredients above, except t-PA, were dissolved in distilled water for injection and the pH of the solution was adjusted to 7.4 by adding sodium hydroxide. To the solution, t-PA was added and then distilled water for injection was added to make the total volume 25 ml. After aseptic filtration, the resulting solution was dispensed into vials, 2.5 ml each, and then lyophilized to prepare a thrombolytic composition.

Example 16

| | |
|---|---|
| t-PA | 50,000,000 IU |
| Sodium chondroitin sulfate | 500 mg |
| Arginine chloride | 1050 mg |
| Tween 80 | 25 mg |
| Mannitol | 500 mg |

The ingredients above, except t-PA, were dissolved in distilled water for injection and the pH of the solution was adjusted to 7.0 by adding sodium hydroxide. To the solution, t-PA was added and then distilled water for injection was added to make the total volume 25 ml. After aseptic filtration, the resulting solution was dispensed into vials, 2.5 ml each, and then lyophilized to prepare a thrombolytic composition.

Example 17

| | |
|---|---|
| t-PA | 50,000,000 IU |
| Sodium chondroitin sulfate | 200 mg |
| Arginine | 2874 mg |
| Sulfuric acid | 1618 mg |
| Tween 80 | 10 mg |
| Purified gelatin | 100 mg |

The ingredients above, except t-PA, were dissolved in distilled water for injection and the pH of the solution was adjusted to 7.0 by adding sodium hydroxide. To the solution, t-PA was added and then distilled water for injection was added to make the total volume 25 ml. After aseptic filtration, the resulting solution was dispensed into vials, 2.5 ml each, and then lyophilized to prepare a thrombolytic composition.

Example 18

| | |
|---|---|
| t-PA | 50,000,000 IU |
| Sodium chondroitin sulfate | 200 mg |
| Lysine chloride | 1593 mg |
| Sodium sulfate | 710 mg |
| Tween 80 | 10 mg |
| Purified gelatin | 100 mg |

The ingredients above, except t-PA, were dissolved in distilled water for injection and the pH of the solution was adjusted to 6.0 by adding sodium hydroxide. To the solution, t-PA was added and then distilled water for injection was added to make the total volume 25 ml. After aseptic filtration, the resulting solution was dispensed into vials, 2.5 ml each, and then lyophilized to prepare a thrombolytic composition.

Example 19

| | |
|---|---|
| t-PA | 50,000,000 IU |
| Sodium chondroitin sulfate | 500 mg |
| Monoethanolamine chloride | 1950 mg |
| Tween 80 | 25 mg |
| Mannitol | 500 mg |

The ingredients above, except t-PA, were dissolved in distilled water for injection and the pH of the solution was adjusted to 7.2 by adding sodium hydroxide. To the solution, t-PA was added and then distilled water for injection was added to make the total volume 25 ml. After aseptic filtration, the resulting solution was dispensed into vials, 2.5 ml each, and then lyophilized to prepare a thrombolytic composition.

Example 20

| | |
|---|---|
| t-PA | 50,000,000 IU |
| Sodium chondroitin sulfate | 25 mg |
| Monoethanolamine chloride | 1950 mg |
| Tween 80 | 25 mg |
| Mannitol | 500 mg |

The ingredients above, except t-PA, were dissolved in distilled water for injection and the pH of the solution was adjusted to 7.2 by adding sodium hydroxide. To the solution, t-PA was added and then distilled water for injection was added to make the total volume 25 ml. After aseptic filtration, the resulting solution was dispensed into vials, 2.5 ml each, and then lyophilized to prepare a thrombolytic composition.

Example 21

| | |
|---|---|
| t-PA | 50,000,000 IU |
| Sodium dextran sulfate | 25 mg |
| Lysine chloride | 910 mg |
| Tween 80 | 25 mg |
| Mannitol | 500 mg |

The ingredients above, except t-PA, were dissolved in distilled water for injection and the pH of the solution was adjusted to 7.0 by adding sodium hydroxide. To the solution, t-PA was added and then distilled water for injection was added to make the total volume 25 ml. After aseptic filtration, the resulting solution was dispensed into vials, 2.5 ml each, and then lyophilized to prepare a thrombolytic composition.

All the preparations shown in Examples 13–21 were fine white lyophilized preparations, readily and completely soluble in a 5% glucose solution or physiological saline, the pH of the solution was neutral, about 7, and the osmotic pressure when reconstituted at a t-PA concentration of 500,000 IU/ml was about 2 which is appropriate for an agent for injection.

Furthermore, t-PA was diluted stepwise at concentrations from 300,000 IU/ml, 100,000 IU/ml, 20,000 IU/ml to 2,500 IU/ml. At all the t-PA concentrations, the dissolution was satisfactory and the solution was stable showing no change in solubility, activity and the apparent molecular weight of t-PA on standing at room temperature for at least 6 hours. Even after the storage at 40° C. for 3 months, these lyophilized preparations were stable showing no change in appearance, solubility on reconstitution, activity and the apparent molecular weight of t-PA.

As demonstrated in the above-mentioned Reference Examples and Examples, without the present invention, it might be difficult to prepare a t-PA preparation which can be soluble at both high and low salt concentrations. On the contrary, according to the present invention, it is possible to dissolve t-PA at a pH near neutral which is the isoelectric point of t-PA, without increasing the salt concentration, and furthermore to dissolve t-PA in a solution with a high salt concentration. Thus the present invention overcomes the restrictions of conventional techniques.

TABLE 1

|  | Additive | Concentration* | Diluent | Dissolution | t-PA Recovery (%) |
|---|---|---|---|---|---|
| Reference Example 2 | Heparin-Na | 0.01% | Saline | Turbid | <20 |
|  |  |  | Glucose solution | Clear | 100 |
| Reference Example 3 | Dextran sulfate-Na | 0.005% | Saline | Turbid | <20 |
|  |  |  | Glucose solution | Clear | 100 |
| Reference Example 4 | Lysine-HCl | 20 mM | Saline | Clear | 100 |
|  |  |  | Glucose solution | Turbid | <20 |
| Reference Example 5 | Monoethanolamine-HCl | 40 mM | Saline | Clear | 100 |
|  |  |  | Glucose solution | Turbid | <20 |
| Example 1 | Heparin-Na + Lysine-HCl | 0.01% 20 mM | Saline | Clear | 97 |
|  |  |  | Glucose solution | Clear | 101 |
| Example 2 | Heparin-Na + Monoethanolamine-HCl | 0.01% 40 mM | Saline | Clear | 96 |
|  |  |  | Glucose solution | Clear | 96 |
| Example 3 | Dextran sulfate-Na + Lysine-HCl | 0.005% 20 mM | Saline | Clear | 98 |
|  |  |  | Glucose solution | Clear | 100 |
| Example 4 | Dextran sulfate-Na + Monoethanolamine-HCl | 0.005% 40 mM | Saline | Clear | 96 |
|  |  |  | Glucose solution | Clear | 102 |

*Concentrations when t-PA was diluted to 0.2 mg/ml.

TABLE 2

| | t-PA concentration | | | | | |
|---|---|---|---|---|---|---|
| | 4 mg/ml | | 0.2 mg/ml | | | |
| Additive | pH | Dissolution | Diluent | pH | Dissolution | DLS* | Supernatant protein (mg/ml) |
|---|---|---|---|---|---|---|---|
| NaPi (60 mM) | 4.2 | Clear | NaPi | 4.19 | Clear | 25 | 0.21 |
| Chondroitin sulfate Na (0.01%) + Monoethanolamine chloride (40 mM) | 6.0 | Clear | S | 6.23 | Clear | 150 | 0.19 |
|  |  |  | G | 6.27 | Clear | 318 | 0.19 |
|  | 7.5 | Clear | S | 8.01 | Clear | 75 | 0.20 |
|  |  |  | G | 7.84 | Clear | 196 | 0.20 |
|  | 9.0 | Clear | S | 8.67 | Clear | 47 | 0.19 |
|  |  |  | G | 8.50 | Clear | 145 | 0.19 |
| sulfate Na (0.01%) + Arginine (30 mM) + Sulfuric acid (30 mM) | 6.0 | Clear | S | 6.53 | Clear | 298 | 0.20 |
|  |  |  | G | 6.66 | Clear | 128 | 0.20 |
|  | 7.5 | Clear | S | 8.09 | Clear | 102 | 0.20 |
|  |  |  | G | 7.98 | Clear | 161 | 0.20 |
|  | 9.0 | Clear | S | 9.05 | Clear | 55 | 0.19 |
|  |  |  | G | 8.98 | Clear | 120 | 0.21 |

Note:
The concentrations of additives are those when t-PA was diluted to 0.2 mg/ml.
The additive NaPI (60 mM sodium phosphate) was used as control in which t-PA solution was diluted without additives using a solution with a pH apart from the isoelectric point of t-PA, where t-PA was to be dissolved sufficiently.
t-PA recovery was estimated to be 100% when the concentration of the supernatant protein was 0.2 mg/ml.
S = physiological saline G = 0.5% glucose solution
* = Diffusion light intensity

TABLE 3

| Dilution rate* | t-PA (IU/ml) | Sodium chondroitin added (mg/mg t-PA) | | | | | | |
|---|---|---|---|---|---|---|---|---|
| | | 0 | 0.022 | 0.055 | 0.11 | 0.22 | 0.55 | 1.1 |
| 1.67 | 300,000 | C | C | C | C | C | C | C |
| 5 | 100,000 | C | C | C | C | C | C | C |
| 10 | 50,000 | T | T | T | C | C | C | C |
| 25 | 20,000 | T | ST | C | C | C | C | C |
| 50 | 10,000 | T | ST | C | C | C | C | C |
| 100 | 5,000 | T | C | C | C | C | C | C |
| 200 | 2,500 | St | C | C | C | C | C | C |

C = Clear
T = Turbid
ST = Slightly turbid
*After reconstitution

TABLE 4

| t-PA (mg/ml) | CS (%) | Ethanol-amine HCl (mM) | Arg-HCl (mM) | Diluent G/S | pH | Specific Activity (x10⁴IU/mg) |
|---|---|---|---|---|---|---|
| 0.2 | — | — | — | G | ca.4.5 | 43.1 |
| 0.2 | 0.01 | 40 | — | G | 6.7 | 46.2 |
| 0.2 | 0.01 | 40 | — | S | 6.7 | 45.8 |
| 0.2 | 0.1 | 40 | — | G | 6.7 | 50.8 |
| 0.2 | 0.1 | 40 | — | S | 6.7 | 53.3 |
| 0.6 | 0.3 | 120 | — | G | 6.7 | 56.5 |
| 0.6 | 0.3 | 120 | — | S | 6.7 | 56.4 |
| 1.0 | 0.5 | 200 | — | G | 6.7 | 48.9 |
| 1.0 | 0.5 | 200 | — | S | 6.7 | 53.5 |
| 0.2 | 0.01 | — | 10 | G | 7.0 | 55.0 |
| 0.2 | 0.01 | — | 10 | S | 7.0 | 41.6 |
| 0.2 | 0.1 | — | 10 | G | 7.0 | 55.5 |
| 0.2 | 0.1 | — | 10 | S | 7.0 | 48.1 |
| 0.6 | 0.3 | — | 30 | G | 7.0 | 53.0 |
| 0.6 | 0.3 | — | 30 | S | 7.0 | 43.8 |
| 1.0 | 0.5 | — | 50 | G | 7.0 | 55.6 |
| 1.0 | 0.5 | — | 50 | S | 7.0 | 56.9 |

CS = Sodium chondroitin sulfate
S = Saline
G = 5% glucose solution
Arg-HCl = Arginine chloride

What is claimed is:

1. A method for increasing the solubility of tissue type plasminogen activator in an aqueous solution, said method comprising adding an anionic polymer or a salt thereof and an amine compound or a salt thereof to said solution.

2. A method for increasing the solubility of tissue type plasminogen activator in an aqueous solution, said method comprising adding an anionic polymer or a salt thereof, an amine compound or a salt thereof and an acid or a salt thereof to said solution.

3. The method as set forth in claim 1 or 2, wherein the anionic polymer is a salt.

4. The method as set forth in claim 1 or 2, wherein the amine compound is a salt.

5. The method as set forth in claim 1 or 2, wherein the anionic polymer or a salt thereof is present at a concentration of 25 or more micrograms per 1 mg of tissue type plasminogen activator.

6. The method as set forth in claim 1 or 2, wherein the amine compound or a salt thereof is present at a concentration of 20 micromoles to 10 micromoles per 1 mg of tissue type plasminogen activator.

7. The method as set forth in claim 2, wherein the acid or a salt thereof is present at a concentration of 20 micromoles to 10 micromoles per 1 mg of tissue type plasminogen activator.

8. The method as set forth in claim 1 or 2, wherein the anionic polymer comprises anion residues selected from the group consisting of carboxyl, carboxymethyl, sulfuric and phosphoric groups.

9. The method as set forth in claim 1 or 2, wherein the amine compound or a salt thereof is selected from the group consisting of monoethanolamine, diethanolamine, triethanolamine, polyethanolamine, arginine, lysine, histidine and salts thereof.

10. The method as set forth in claim 2, wherein the acid or a salt thereof is selected from the group consisting of oxalic acid, hydrochloric acid, sulfuric acid, phosphoric acid, pyrophosphoric acid, citric acid, tartaric acid, malic acid, maleic acid, glucaronic acid, glutaric acid, lactic acid, adipic acid, ascorbic acid and the salts thereof.

* * * * *

UNITED STATES PATENT AND TRADEMARK OFFICE
CERTIFICATE OF CORRECTION

PATENT NO. : 6,051,223
DATED : April 18, 2000
INVENTOR(S) : Shimazaki et al.

It is certified that error appears in the above-identified patent and that said Letters Patent is hereby corrected as shown below:

Figure 3,
Drawings, in the legend along the right hand margin of the graph, change the open ○ and solid ● "o's" to open △ and solid ▲ triangles.

Column 3,
Line 61, change "weekly" to -- weakly --.
Line 63, delete "ofpH" insert -- of pH --.

Column 5,
Line 24, delete the comma (,) after "the".
Line 30, "solution-added" should be -- solution added --

Column 7,
Line 1, delete "a" insert -- an --.
Line 57, insert -- of -- after "combination".

Column 8,
Line 42, delete "ofsulfuric" insert -- of sulfuric --.

Column 9,
Line 29, delete "1mg" insert -- 1 mg --.
Line 61, delete "physico-chemical" insert -- physico chemical --.

Column 10,
Line 22, delete "a" (second occurence) insert -- an --.

Column 16, claim 6,
Line 23, delete "micromoles" second occurrence and insert -- millimoles --.

UNITED STATES PATENT AND TRADEMARK OFFICE
CERTIFICATE OF CORRECTION

PATENT NO. : 6,051,223
DATED : April 18, 2000
INVENTOR(S) : Shimazaki et al.

It is certified that error appears in the above-identified patent and that said Letters Patent is hereby corrected as shown below:

<u>Column 16, claim 7,</u>
Line 27, delete "macromoles" insert -- millimoles --.

Signed and Sealed this

Thirteenth Day of November, 2001

Attest:

*Nicholas P. Godici*

NICHOLAS P. GODICI
*Acting Director of the United States Patent and Trademark Office*

*Attesting Officer*